United States Patent [19]

Quintana et al.

[11] Patent Number: 5,030,554
[45] Date of Patent: Jul. 9, 1991

[54] CONSERVATIVE WHOLE BLOOD SAMPLE PREPARATION TECHNIQUE

[75] Inventors: Jorge A. Quintana; Thomas R. Russell, both of Miami; Ronald D. Paul, North Miami Beach; Timothy J. Fischer, Plantation, all of Fla.

[73] Assignee: Coulter Corporation, Hialeah, Fla.

[21] Appl. No.: 128,668

[22] Filed: Dec. 4, 1987

[51] Int. Cl.$^5$ .................... A61K 35/14; C12Q 1/02; G01N 1/00
[52] U.S. Cl. .................... 435/2; 435/7.24; 435/29; 435/34; 436/166; 436/172; 436/175
[58] Field of Search .................... 435/2, 29, 34, 7; 436/17, 166, 172, 175, 522

[56] References Cited

U.S. PATENT DOCUMENTS 4,521,518  6/1985  Carter et al. .................... 436/10
4,637,986  1/1987  Brown et al. .................... 436/10

OTHER PUBLICATIONS

Nelson, D. A. et al., "Basic Methadology", in *Clinical Diagnosis and Management by Laboratory Methods*, (Henry, J. B. et al., ed), W. B. Saunders, Philadelphia, pp. 578–592 and 623–625 (1984).
Caldwell, Charles W. et al., "A Rapid, No-Wash Technic for Immunophenotypic Analysis by Flow Cytometry", A.J.C.P., vol. 86, No. 5, pp. 600–607 (1986).
Caldwell, Charles W. et al., "Fluorescence Intensity as a Quality Control Parameter in Clinical Flow Cytometry", A.J.C.P., vol. 88, No. 4, pp. 447–456 (1986).

*Primary Examiner*—Esther L. Kepplinger
*Assistant Examiner*—Toni R. Scheiner
*Attorney, Agent, or Firm*—Gerald R. Hibnick

[57] ABSTRACT

The method of this invention is directed to the rapid preparation of a whole blood sample for photooptical analysis. In the preferred embodiments of this method, a whole blood sample, lytic reagent system and immunological stain (optional) are contacted with the sample in a common reaction vessel (i.e. cuvette or test tube), with gentle asymmetric vortex mixing, so as to maintain the particulate matter of the sample at an essentially homogeneous concentration throughout the sample. An aliquot of the contents of the reaction vessel can, thereafter, be analyzed for identification and/or quantification of the analyte of interest. This process is conservative of the various endogenous constituents of the sample since virtually all of the manipulative steps involved in the preparation of the sample occur within a common vessel and any excess (unconsumed or unreacted) reagents and stain need not be separated from the sample during such preparation, thus, avoiding the multiple wash steps traditionally associated with this process. This process is uniquely applicable to the conservative preparation of aged whole blood samples (samples in which the endogenous nutrients have been essentially completely consumed) and whole blood samples from diseased state patients wherein the disease is manifest by changes in the morphology, total number and/or relative concentration of one or more of the lymphocyte subpopulations (i.e. B and/or T-cells).

12 Claims, 3 Drawing Sheets

FIG. 1
FIG. 2
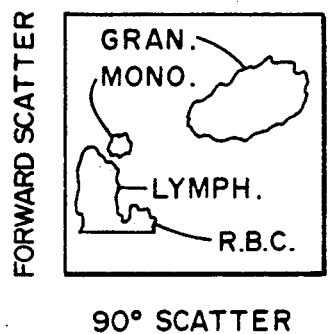
FIG. 1A
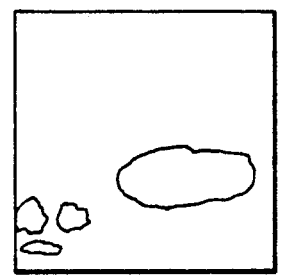
FIG. 2A
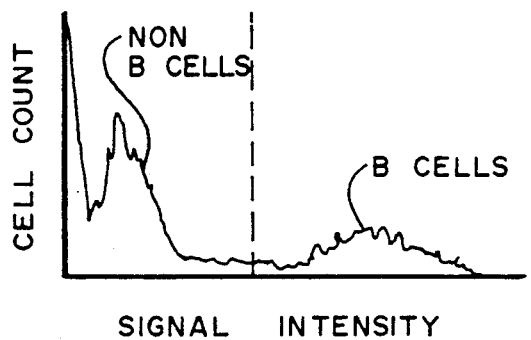
FIG. 1B
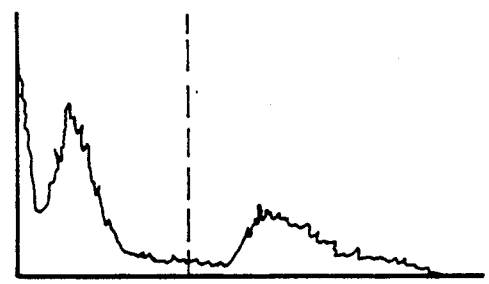
FIG. 2B
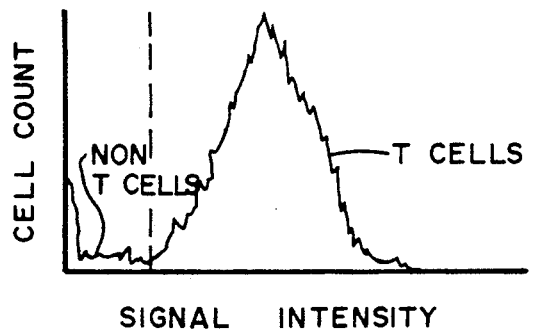
FIG. 1C
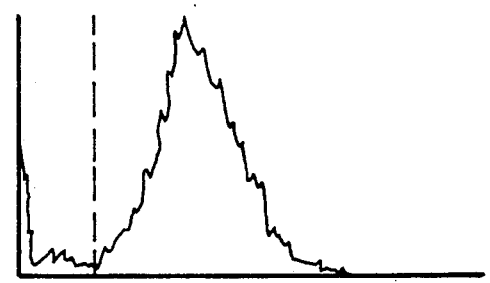
FIG. 2C FIG. 3
FIG. 4
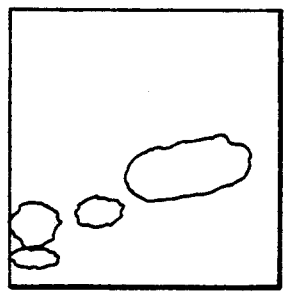
FIG. 3A
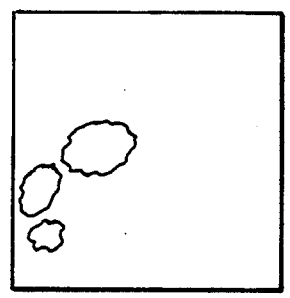
FIG. 4A
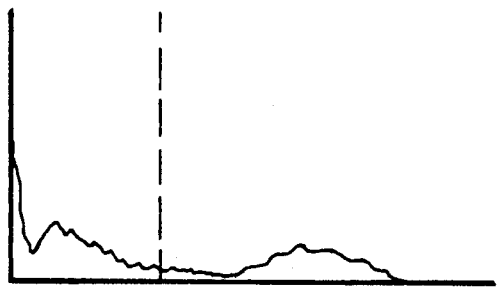
FIG. 3B
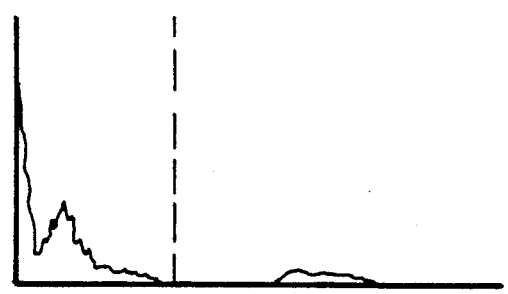
FIG. 4B
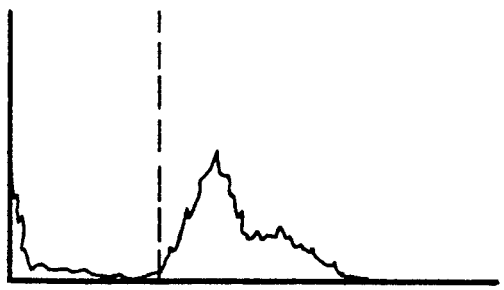
FIG. 3C
FIG. 4C FIG. 5
FIG. 6
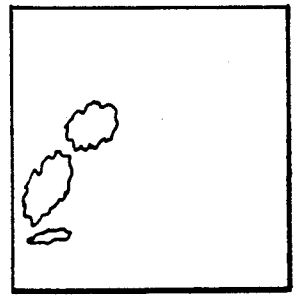
FIG. 5A
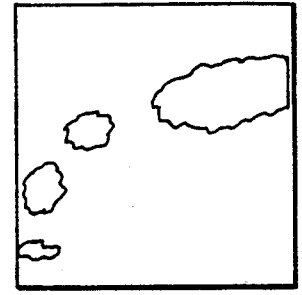
FIG. 6A
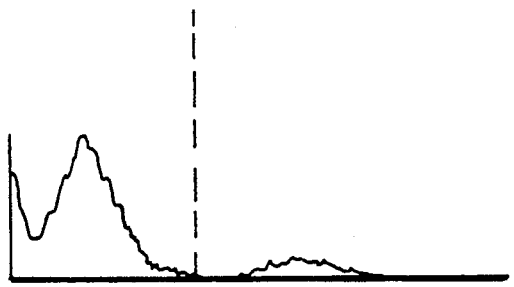
FIG. 5B
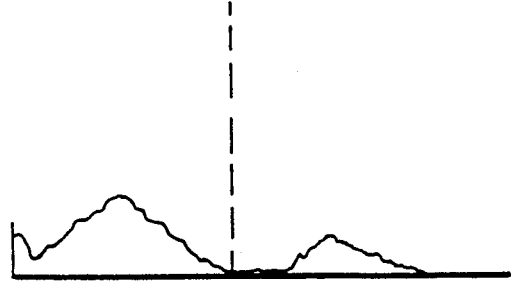
FIG. 6B
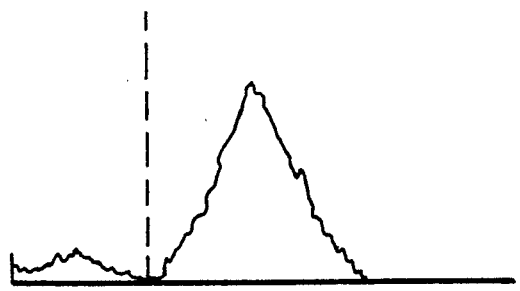
FIG. 5C
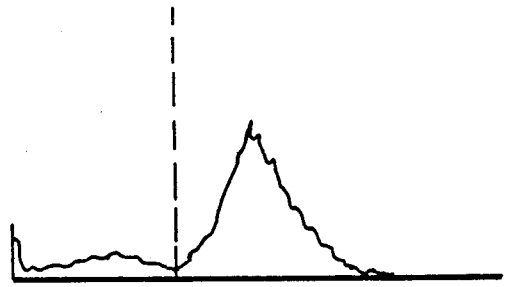
FIG. 6C

CONSERVATIVE WHOLE BLOOD SAMPLE PREPARATION TECHNIQUE

BACKGROUND OF THE INVENTION

1. Field of the Invention

This invention is directed to a method. More specifically, this invention concerns a unique process for the rapid preparation of particulate analytes, notably cells, cell organelles and the like, for analysis by photooptical means. This process is particularly well suited for analysis of cellular analytes which are present in small concentrations and/or where a change in their relative proportion to another cell population is diagnostically significant. The ability of this process to afford such advantage over the more traditional techniques is based upon the conservative nature of the preparation process. The term "conservative" as used herein is intended as descriptive of the ability of this process to preserve virtually all of the blood components, with the exception of erythrocytes, for later analysis. The integrity of the sample, with respect to the conserved components, also provides the first truly reliable means for the establishment of standards against which other samples can be measured. This process is particularly well adapted to analysis of aged samples of whole blood, and to blood samples from disease state patients, wherein cell integrity is difficult to maintain and thus an accurate analysis heretofore impossible. This process is particularly well suited for rapid preparation of whole blood samples for analysis by flow cytometry.

2. Description of the Prior Art

The traditional techniques for the isolation and staining of the leukocyte fraction of whole blood has typically involved numerous physical manipulations of the sample and an inordinate number of wash steps. As has been appreciated and reported in the technical literature, these traditional techniques inherently result in some finite depletion of the leukocyte population from the sample; at least some alteration in the gross morphology of the leukocyte population which remain in the sample; at least some alteration in the markers on the surface of the leukocyte population; and, at least some displacement of the strain on the surface of the cell population of interest.

The techniques which have been used up to now in the preparation of leukocytes from whole blood samples for subsequent analysis have traditionally involved: (1) the preparation of a buffy coat fraction by controlled centrifugation of the whole blood sample, followed by staining with a fluorochrome labelled conjugate; (2) concurrent treatment of a whole blood sample with a lytic reagent and a fluorochrome labelled conjugate; or (3) the preparation of a buffy coat fraction by controlled centrifugation of the whole blood sample and thereafter subjecting the buffy coat sample to further enrichment by Ficoll-Paque density gradient centrifugation. Such enrichment permits the recovery of an interfacial layer containing enriched mononuclear cells which are thereafter stained with a fluorochrome labelled conjugate.

Each of the above preparative procedures is labor intensive, requires repeated physical manipulation of the fraction containing the leukocytes of interest and is time consuming. Where conventional centrifugation techniques are used to obtain an enriched leukocyte sample, cell loss will invariably take place and, thus accurate determination of the relative concentration of the cellular population of interest is virtually impossible.

The shortcomings in the above procedures have been recognized for some time and at least one alterative has been proposed in the technical literature, articles by Caldwell, appearing in A.J.C.P., vol. 88:4 (1987) pp. 447-456; and et al, A.J.C.P., Vol. 86:5 (1986), pp. 600-607. The Caldwell articles, however, focus only upon one facet of this problem, which he believes to be the principle detractor from prior procedures. More specifically, Caldwell emphasizes that excessive washing of the leukocytes samples subsequent to staining and prior to analysis can introduce analytical error into the analysis, especially where leukocytes are observed in certain classes of diseased patients. Caldwell suggests adoption of a "no wash" technique to reduce processing time and analytical error which is inherent in the extensive manipulation treatment of the leukocyte sample prior to its ultimate analysis. The "no wash" technique proposed by Caldwell involves retention of the traditional techniques for preparation of an enriched lymphocyte fraction (i.e., Ficoll-Paque density gradient centrifugation, which itself contemplates multiple wash steps for removal of the Ficoll-Paque reagents). The enriched sample of lymphocytes is, thereafter, stained with a fluorochrome dye conjugated to a monoclonal antibody. Caldwell's improvement resides in the observation of enhanced fluorescence intensity in both background and positive peaks of a histogram when the unbound conjugate is allowed to remain in the sample. Caldwell attributes this observation of enhanced fluorescence intensity to his elimination of the wash steps after staining. He hypothesizes that the elimination of such wash step is less disruptive upon the stained lymphocyte fraction, thus, enabling preservation of the immunochemical bond between the conjugate and the surface markers on the cell population of interest. As is clearly evident from review of Caldwell's "no wash" procedure, the repeated trauma of mixing, vortexing and centrifugation is only somewhat reduced.

The "enrichment" of the leukocyte sample through the use of lytic reagents has not, up to now, proven to be a viable alternative to the more traditional centrifugation/density gradient techniques for partitioning the whole blood sample into its various fractions. The reason for this limitation is the inablity of prior lytic reagents to effect hemolysis of the erythrocyte fraction of whole blood without also traumatizing the leukocyte fraction of the sample. These lytic reagents typically cause both gross and subtle morphological changes in the leukocyte fraction and alternation in the surface markers on such cells. In the limited number of instances where lytic reagents have been used with some measure of success, additional reagents were required to be added to the sample to protect the leukocytes from lysis by the lytic reagent, see for example, U.S. Pat. No. 4,637,986 (to Brown, et al). As is evident from the review of the Brown patent, the physiological environment of the sample is modified dramatically by the addition of both lytic reagent and the solutes which are used to protect the leukocytes from lysis by the lytic reagent. The samples prepared in accordance with Brown's reagents and technique can be subjected to analysis by flow cytometry where differation of the three principle sub-populations is accomplished by conventional light scattering measurements. Because of the alteration in the physiological environment of the sample, the integrity and immunochemical response of the surface markers on the leukocytes of the samples is altered as well. Thus, refinement in the analysis of the leukocyte fraction by immunochemical techniques is precluded. Moreover, where the leukocyte fraction is from a sample which is "aged" (not fresh) or a diseased patient sample, the sensitivity of the leukocytes to such harsh treatment is increased dramatically, thus, further limiting the usefulness of the Brown reagents and technique.

As is evident from the above discussion, both the physical and chemical trauma which can be effected upon the leukocyte fraction by the above procedures, is likely to damage a number of the cells within this fraction. Even more unfortunate, these procedures are more destructive of the leukocytes (i.e. lymphocytes) of disease state samples, Accordingly, the ability to analyze and monitor such disease state samples by traditional enrichment/staining techniques is severely limited. Where such analysis are to be performed, the more traditional centrifugation/density gradient enrichment protocols are preferred, since they are somewhat less disruptive of the lymphocytes than the effects of the lytic reagents.

The enhancement in accuracy and sensitivity observed by Caldwell in his "no-wash" procedure represents a step in the appropriate direction, however, further improvement is obviously necessary, particularly where relative cell population determinations are critical to an accurate analysis of the patients conditions. As is evident from the above discussion, none of the prior art techniques, even that described by Caldwell, provide a complete solution to this problem, since virtually every procedure, even those utilizing lytic reagents, occasion a statistically significant loss or destruction in one or more of the sub-populations of leukocytes; and at least 1 hour total preparation time. This loss is statistically more significant in dealing with an aged sample (i.e. a sample essentially totally deficient in endogenous nutrient) and disease state samples because of the relatively higher sensitivity of the nutritionally deprived cells, and cells indicative of the disease state of lysis by physical and chemical trauma.

SUMMARY OF THE INVENTION

The objective of this invention are to provide a method and system for the conservation of the cellular analytes of content of a sample to insure that the analysis thereof accurately reflect both the number of the cellular analytes of interest in the sample and; where appropriate, the relative concentration of such analytes to other cells of the sample. Thus, this invention is concerned with preparation of the sample so as to insure that virtually all diagnostically relevant components of the sample are conserved. In the analysis of whole blood, the diagnositcally relevant component of particular interest is the non-erythrocyte fraction. This invention provides the ability to effectively isolate and yet effectively conserve the non-erythrocyte fraction without the washing and multiple transfer steps traditionally associated with that process. In the preferred embodiments of this invention, a whole blood sample is placed in an incubation chamber. The incubation chamber of choice is the same type of vessel which is used in the instrument selected for analysis of the sample. This process of preparation of the sample departs from the norm in that virtually all contact of the sample with reagents is performed in the incubation chamber and the intimate interaction of the sample and such reagents is assured by asymmetric vortexing of the content of the chamber at the appropriate intervals, frequency and for the appropriate duration. By precisely controlling the reagent additions, reaction environment and the physical forces acting upon the sample, it is now possible to prepare a whole blood sample, (even aged or disease state samples) without washing or statistically significant in any of the diagnostically significant non-erythrocyte blood components.

More specifically, this method and system provides a conservative method and system in which the mixing dynamics and reagents effect rapid and essentially complete hemolysis of the erythrocyte fraction of a whole blood sample while maintaining the non-erythrocyte fraction of the sample in its essentially native physiological state. This method and system are, thus, compatible with the selective staining of one or more sub-populations of the leukocyte fraction, either prior to, or concurrent with, hemolysis of the erythrocytes. Subsequent to such staining, the sample can be subjected to analysis by semi-automated or automated techniques (i.e. flow cytometry) for identification and quantification of the cell populations of interest. This process of enrichment and standing of the leukocyte fraction of the sample can be performed within about sixty (60) seconds or less, provides improved clustering of the various sub-populations of the leukocytes within the sampler; and, is conservative of the integrity and of the total number of leukocytes present in the sample.

In one of the preferred embodiments of this invention, the whole blood sample and stain are initially combined in an incubation/mixing chamber. A 12×75 mm test tube, of the type commonly used with the EPICS brand flow cytometer (available from Coulter Electronics), is generally suitable for this purpose. The test tube and its contents can then be aggitated on a suitable mixing device (i.e. Q-PREP ™ mixer also available from Coulter Electronics). This mixer has the capability for continuous and controlled mixing of the fluid contents of the test tube and the automated introduction of additional reagents at the appropriate pre-programmed interval. Initially, an immunological stain can be contacted with the whole blood sample in the incubation chamber, accompanied by gentle, asymmetric vortex mixing. After a suitable incubation period, generally less than sixty (60) seconds, a differentiation effective amount of a novel lytic reagent is contacted with the sample in the chamber and, thereafter its lytic activity substantially retarded by the introduction of a suitable quench. The entire process of staining, lysing of the erythrocytes and quenching of the activity of the lytic reagent is performed without prior physical isolation of the cells from one another, without transfer of the cells of the sample from one vessel to another and without the need for removal of unreacted stain and/or unconsumed reagents from the incubation chamber prior to analysis or measurement of the sample. The stained leukocyte fraction can now be subjected to further analysis on instrumentation designed for that purpose (i.e. EPICS Model C or PROFILE flow cytometer). The analysis of the sample on such instrumentation enables the generation of a histogram with well-defined clustering of the stained leukocyte fraction of interest.

BRIEF DESCRIPTION OF THE DRAWINGS

FIG. 1 is a scattergram of the stain sample of Example I.

FIG. 2 is a scattergram of the stain sample of Example II.

FIG. 3 is a scattergram of the stain sample of Example III.

FIG. 4 is a scattergram of the stain sample of Example IV.

FIG. 5 is a scattergram of the stain sample of Example V.

FIG. 6 is a scattergram of the strain sample of Example VI.

DESCRIPTION OF THE INVENTION INCLUDING PREFERRED EMBODIMENTS

As indicated above, in somewhat abbreviated fashion, the method and system of this invention are unique in a number of significant respects: (a) the ability to sequentially or concurrently rapidly stain and enrich the non-erythrocyte fraction of a whole blood sample; (b) the conservation of the morphology and total number of leukocytes originally present in the sample; (c) the preservation of the immunochemical interaction between the stain and the characteristic cellular components of the cell population of interest; (d) the preservation of the stained/enriched sample for up to twenty-four (24) hours prior to analysis without material alteration of the characteristics size and/or shape of the subpopulation of interest and, (e) the compatibility of the reagents utilized in the staining sequence with the reagents used in both lytic sequence and quenching sequence so as to eliminate the neccessity of washing of the sample between each such processing step.

Preliminary to entering into a detailed discussion of the method and system of this invention, it will be helpful to initially define a number of terms and phrases.

The terms "stain" and "staining" as used herein are intended as descriptive of a process for identification of a specific cell population of interest so as to permit its differentiation from other cells which are also generally present in a sample undergoing analysis.

The term "conservative" as used herein is intended as descriptive of both the conditions and manipulative steps of the method of this invention which preserves not only the total number of leukocytes originally present in the sample, but also their gross morphology and their immunochemical reactivity. Such conservation is achieved without prior fixation of the leukocyte population, but can include fixation subsequent to such preparation.

The term "nutative" and phrase "nutative motion" as used herein is intended as descriptive of an asymmetric or eccentric mixing action of a reaction vessel, wherein the sample and various reagents (stain, lytic reagent, quench and fixative-if any) are maintained in a mild state of agitation. This type of movement of the reaction vessels cause the fluid contents of the vessel to asymmetrically distribute itself within the vessel, rising up to a greater height on one side of the vessel than the other. Because of this asymmetry, the vortex which forms in the vessel does not behave in the traditional manner; and, fluid mixing appears to occur as a result of an essentially circular, planar motion. Mixing equipment suitable for use in the method and system of this invention is available from Coulter Electronics of Hialeah, Florida under the Q-PREP brand name.

The term "enrichment" as used herein is intended as descriptive, in the context of this invention, of the relative increase in ease of identification (i.e. "visibility") of the leukocyte population of a whole blood sample upon lysis of the erythrocyte fraction of the sample; and, in the context of the prior art, the physical separation of the leukocyte population (i.e. buffy coat) from the other constituents of the whole blood sample.

As noted previously in the discussion of the relevant prior art, the preferred technique for staining of the leukocyte fraction involves an immunochemical interaction of an indicator/antibody conjugate with a surface marker which is characteristic of the cell fraction of interest. The relative avidity of the conjugate for a specific surface marker of interest, can vary depending upon the precise location and conformation of the epitopic site on the cell surface. Where the cell population of interest, or cell count, is indicative of a disease state, these cells tend to be more fragile and, thus their interaction with the stain more sensitive to physical trauma and to chemical imbalance in the sample environment. Thus, the abbreviated contact with the lytic reagent (generally less than ten (10) seconds) and the subsequent restoration of the ionic balance of the leukocyte fraction (by the addition of the quench) is conservative of both the total numbers and of the qualities of the cells of interest and, thus, facilitates their subsequent identification by immunochemical techniques. Since there is typically a hiatus between the time at which the sample is enriched and stained and its subsequent analysis, the sample is preferably contacted with a fixative to preserve both the physical size and shape of the leukocyte fraction of interest. Such fixations must of course be compatible with the prior enrichment/staining procedures and be further compatible with the analytical means selected for the determination/measurement of the relative concentration of the cell population of interest. Where the analytical method of choice is flow cytometry, the fixative selected must, of course, not exhibit any native or autofluoresce at the wavelength of excitation energy of the fluorochrome label of the conjugate stain; or, at the emission wavelength of fluorochrome stain. Other requirements of such fixatives are to be more fully discussed hereinafter in the context of the discussion of the reagent system. The preferred fixative is paraformaldehyde.

In the practice of the method of this invention, peripheral blood is aseptically collected by standard venipuncture techniques in vacuum tubes containing an anticoagulant (i.e. EDTA or heparin). The specimen is, thereafter, transferred to an incubation/mixing chamber of the type typically used in conjunction with the analytical/measuring device of choice. In the semi-automated equipment contemplated for practice of this method of invention (i.e. Q-PREP ™ sample preparation device), the sample is then contacted with appropriate quantities of the stain, the lytic reagent and fixative. During this period of contact with these various materials, the sample is maintained in a continuous state of mild agitation. In one of the preferred embodiments of this invention the stain is combined with a whole blood sample prior to addition of the lytic reagent system and fixatives. The activity of the lytic reagent is subsequently substantially retarded by the addition of a separate quench. The quench is added within about ten (10) seconds after initial contact of the sample with the lytic reagent. The staining is allowed to continue, with the entire process being completed within about ninety (90) seconds. The fixative (optional) is preferably added at the conclusion of the staining cycle and subsequent to the addition of the quench. In an alternative embodiment of this invention, the staining of the leukocyte fraction of interest can precede enrichment of the sample. In this embodiment of the invention, the stain is simply added to the whole blood sample and allowed to interact with the cellular fraction of interest. Such interaction occurs, under mild agitation, for approximately 15 to 60 seconds, prior to addition of the lytic agent, quench and fixative (optional).

The complement of chemicals, which are employed to effect both hemolysis of the erythrocyte fraction of the sample and subtle modification of the leukocyte fraction, and thereby facilitate their subsequent isolation, identification and/or analysis, are collectively referred to as the "lytic reagent system". In the context of this invention, such system includes a lytic reagent and a companion quench, which is formulated for substantially retarding the lytic activity of the lytic reagent and restoring the ionic balance of the sample.

The preferred lytic reagent which is suitable for use in the method and system of this invention comprises an aqueous solution containing a differentiation effective amount of a lytic reagent comprising a water soluble, organic carboxylic acid having a pK value $>3.0$, a pH in the range of from about 2.6 to 4.0 and a counterion which does materially alter the ionic strength of the treated sample. The most preferred lytic reagents are selected from the group consisting of formic acid, acetic acid and their respective mixtures. In the preferred embodiments of this invention, these lytic reagent mixtures will comprise formic acid, as the major functional component, with the acetic acid being present in only minor amounts, if at all. The phrase "differentiation effective amount" is used through this disclosure as indicative of a concentration of lytic reagent which is not only effective for hemolysis of the erythrocyte fraction of the sample, but also effects subtle changes in the leukocyte fraction to facilitate their subsequent isolation, identification and/or analysis.

The lytic reagent employed in the method and system of this invention comprises an aqueous solution containing surprisingly low concentrations of the lytic reagent (preferably less than 1.0% by volume). The lytic reagent is preferably formic acid, acetic acid or mixtures of formic and acetic acid in which formic acid is the predominant functional component. This aqueous solution is prepared by simple addition of the lytic reagent to deionized water. The amount of lytic reagent added to this diluent is sufficient to prepare a solution containing from about 0.05 to about 0.5% (v/v) solution. In the preferred embodiments of this invention, the concentration of lytic reagent will range from about 0.1 to about 0.25% (v/v).

Where the lytic reagent comprises a mixture containing both formic and acetic acid, the acetic acid is preferably only present as a partial replacement for a definitive amount of formic acid and then only at a concentration in the range of from about 0.05 to 0.10% (v/v).

The lytic reagent system can also contain other traditional additives, to the extent their presence is not otherwise incompatible with the primary functional components of the system (i.e. anti-microbial preservatives, such as sodium omadine).

This lytic reagent system can be combined with a whole blood sample by simple manual or automated addition, the lytic reagent and sample allowed to briefly interact in a suitable incubation chamber, and the action of the lytic reagent substantially retarded by addition of a suitable quench. The quench, to be effective in this environment, must, thus, be capable of retarding the lytic activity of the lytic reagent immediately upon its addition to the aqueous mixture contained in the blood sample and the lytic reagent. The precise formulation of the quench can vary, depending upon the composition of the lytic reagent system and other fluids which may be dictated by the requirements of the analytical measurement instrument. The quench is typically an aqueous solution containing soluble salts which are both effective to substantially retard and/or substantially neutralize the lytic activity of the lytic reagent and restore the ionic balance to the sample. This restoration of the ionic balance will extend the longevity of the surviving cells and permit subsequent analysis on equipment which requires that the sample be electrically conductive (contain electrolytes), as for example with an EPICS C ® flow cytometer.

A quench which is suitable for use in conjunction with the lytic reagent composition can, and usually will, contain any combination of at least two of the following four ingredients: sodium chloride, sodium sulfate, sodium bicarbonate, sodium carbonate; and, in addition, sodium azide as a preservative. The effectiveness of the quench upon the lytic reagent in the context of the method and system invention is determined by its ability to rapidly reduce the lytic activity of the formic acid, acetic acid and the mixtures of formic and acetic acid. As noted above, the method and equipment utilized in the differentiation of the leukocyte subpopulation can also place certain requirements (i.e. conductivity, pH, etc.) upon the precise formulation of the quench. More specifically, when such differentiation is performed in a focused flow aperture analysis system, the composition and volume of quench can be critical to optimal separation (differentiation) of the five (5) leukocyte subclasses from one another. In this type of analysis system, the ionic balance of the quench must also be adjusted to obtain a satisfactory conductivity match of the lysed blood sample to the sheath fluid. In the preferred quench formulation, the major ionic species and their relative ratio in the lysed-quenched blood sample should be essentially the same as the major ionic species and their relative ratio in the sheath fluid. The relative concentration of the functional components of the quench, which is to be used in conjunction with the lytic reagent system of this invention, will range from about 1 to about 3% (w/v) sodium chloride, about 0.25 to about 0.8% (w/v) sodium carbonate or bicarbonate, and about 2 to about 5% (w/v) sodium sulfate. The precise relative quantities of ingredients of the optimum quench are generally determined empirically; the objectives of such adjustment being to attain the pH of the lysed blood sample within the range of from about 6.0 to about 7.5, and a final osmolality of the stabilized lysed blood sample in the range of from about 300 to about 330 mOs. It has been previously observed, in a focused flow aperture system, that optimal clustering of the leukocyte subclasses is achieved by adjustment in the osmolality of the final blood sample to about 310 mOs. The essentially complete neutralization of the acidity of the lysed sample with an alkaline quench can be critical to a focused flow aperture analysis system. Components of the sample (i.e. fibrin and platelets) are pH sensitive and can form aggregates under acidic conditions which can potentially interfere with differential analysis (i.e. noise) or physically obstruct the aperture of a focused flow aperture system. These considerations with respect to pH adjustment may also prove critical in other analytical/measurement environments.

In the preferred embodiments of this invention, the duration of effective contact of the lytic reagent and the blood sample (from the time the two are combined, to the time when the quench is added), must be less than ten (10) seconds, and most preferably six seconds or less. The interval of reactive contact of the lytic reagent and blood sample as specified above, presumes such reactive contact occurs at room temperature (~18°–28° C.).

The stain which is used in the method and system of this invention comprises an indicator which has been conjugated to a protein which is specific for binding to an epitope on the cell surface of a cellular analyte of interest (i.e. B-lymphocytes and T-lymphocytes). Antibodies specific for leukocytes surface markers are available from a number of commercial sources. In the preferred embodiments of this invention a monoclonal antibody is the reagent of choice. Monoclonals which are specific for surface markers on T-cell and B-cells can be readily obtained commercially. In a number of instances these same monoclonals antibodies which have been conjugated to an appropriate indicate (flurorchrome) and the resulting conjugates also commercially available.

A series of analysis were made in the evaluation of the method and reagent system of this invention by comparison to prior art techniques used in enrichment and staining of a specific leukocyte population of interest (B- and T-cells). In each instance, the whole blood sample was common to each, as was the method/equipment for measurement of the specific cell population of interest. The technique for separation/enrichment of the leukocyte fraction followed the protocol established for each of the reagent systems designed for that purpose (Examples I-V). The method and reagent system of this invention is illustrated in Example VI. In each of these Examples, the analysis of the enriched sample was conducted on an EPICS Model C flow cytometer, (Coulter Electronics, Hialeah, Fla.) following the standard operating protocol for this instrument. The results of each analysis is depicted in a series of scattergrams, FIGS. 1, 2, 3, 4, 5 and 6; with FIGS. 1-5 representing the prior art and FIG. 6 the method/reagent system of this invention.

EXAMPLE I

The separation media and method used in the preparation of the sample for this Example involved separation/enrichment of the leukocyte fraction by traditional lysis techniques, followed, thereafter by staining with a fluorochrome labeled antibodies which are specific for B and T cells, respectively; Ortho Diagnostic System, procedure for preparation and staining of mononuclear cells for analysis on ORTHO SPECTRUM III Laser Flow Cytometry System, CYTOFLUOROGRAF ™. Following preparation of the sample, the relative concentration of B and T cells is determined in an EPICS Model C flow cytometer. FIG. 1A represents a scattergram of the leukocyte sub-populations of whole blood sample from a healthy donor. FIG. 1B represents the relative B-cell concentration (12.20%) FIG. 1C represents the relative T-cell concentration (83.30%).

EXAMPLE II

Sample preparation involved lysis of erythrocytes with a detergent in accordance with the procedures described for the reagent system marketed under the Immunolyse label by Coulter Immunology. Sample analysis is performed in the same manner as for the sample of FIG. 1 FIG. 2A represents a scattergram of the leukocytes sub-population of a whole blood sample from the same healthy donor as depicted in the scattergram of FIG. 1. FIG. 2B represents the relative concentration of B-cells in the sample. FIG. 2C represents the relative concentration of T-cells in the sample. Note the variations in results in comparison of reported relative concentration of B cells and T cells with the values reported for the analysis conducted in accordance with FIG. 1.

EXAMPLE III

Sample preparation involved lysis of erythrocytes with diethylene glycol in accordance with the procedures described for the reagent system marketed under the FACS label by Becton-Dickinson. FIG. 3A represents a scattergram of this leukocyte sub-population of a whole blood sample from the same healthy donor as in FIGS. 1A and 2A. FIG. 3B is an enhanced scattergram representing the relative concentration of the B-cells in sample (19.04%). FIG. 3C is an enhanced scattergram representing the relative concentration of the T-cells in the sample (69.17%). Note the lack of correlation of the results with the scattergram of FIGS. 1 and 2. Moreover, the relative concentration B to T cells has also shifted dramatically, indicating that the sample preparation (lysis of RBC's with diethylene glycol) is unduly harsh upon T cells.

EXAMPLE IV

Sample preparation involved density gradient separation of primarily lymphocyte and monocyte sub-populations. This procedure is acknowledged to be highly techician dependant and reportedly prone to substantial cell losses. FIG. 4A represents a scattergram of the leukocyte sub populations of a whole blood sample from the same healthy donor as in FIGS. 1A, 2A and 3A. FIG. 4B is an enhanced scattergram representing the relative concentration of the B-cells in such sample (4.64%). FIG. 4C is an enhanced scattergram representing the relative concentration of the T-cell in such sample (88.55%). Note the lack of correlation of the results with the scattergrams of FIGS. 1, 2 and 3. Moreover, the relative concentration of B cells to T cells has also dramatically shifted indicating that repeated washing and physical manipulation is more traumatic to B cells than T cells.

EXAMPLE V

The procedures of Example IV is repeated except that the unreacted stain is allowed to remain in the incubation chamber and the analysis conducted as specified per Caldwell et al "no wash". The scattergram of FIG. 5A represents the leukocyte subpopulation which are capable of differentiation. FIG. 5B is an enhanced scattergram representing the relative concentration of the B-cells (8.14%). FIG. 5C is an enhanced scattergram representing the relative concentration of the T-cells (87.75%). Note the increased relative concentration of the B-cell population, thus, confirming the Caldwell et al observation regarding the advantages of elimination of the wash step following staining of the sample.

EXAMPLE VI

Sample preparation involved rapid (less than 90 seconds total elapsed time) staining/lysis/quench/fixation of the sample. Sample preparation involved the automated dispensing/mixing of the following reagents, in prescribed sequence, with the a whole blood sample from the same donor as in Examples I-V.

| I. Materials | |
|---|---|
| 1. Lyse formulation: | 1.2 mL formic acid |
| | 0.2 mL sodium omadine (40) |
| | 998.6 mL deionized water |
| 2. Quench Formulation: | 31.30 grams soduim sulfate |
| | 14.50 grams sodium chloride |
| | 6.00 grams dodium carbonate |
| | 1 liter deionized water |
| 3. Fixative: | 6.05 grams TRIS (HCL) buffer |
| | 10.00 grams paraformaldehyde |
| | 00.05 mL sodium hydroxide (50%) |
| | 1 liter deionized water |
| 4. Stain: | Becton-Dickinson |
| | Immunocytometry Systems |
| | G1-FITC |
| | HLE-FITC |
| | Coulter Immunology Division |
| | MIG-FITC  TY-RD1 |
| | MIG-RD1  T1-FITC |
| | T8-FITC  B1-FITC |

The device (Q-PREP TM available from Coulter Electronics, Hialeah, Florida) used in the programmed addition of the stain, lytic reagent system and fixative delivered a pre-set amount of each of these reagents at the appropriate interval during mild agitation of a 25×75 mm test tube operating on the following cycle:

(a) addition of fluorochrome labeled antibody to sample
(b) mild agitation of sample stain for 60 seconds
(c) addition of lytic reagent to stained sample
(d) agitate for 6 seconds
(e) addition of quench
(f) agitate for 10 seconds
(g) addition of fixative
(h) place test tube in flow cytometer and analyze for relative population of B-cells and T cells.

FIG. 6A is a scattergram of the leukocyte sub-population of a whole blood sample from the same healthy donor as in FIGS. 1A, 2A, 3A, 4A and 5A. FIG. 6B is an enhanced scattergram representing the relative concentration of the B-cells in such sample (19.79%). FIG. 6C is an enhanced scattergram representing the relative concentration of T-cells in such sample (76.97%). Note the relating high concentration of B-cells indicating that the method and reagent system of this invention are effective in the identification of the relevant sub-population of interest and that this technique is efficacious with minimal technician involvement.

What is claimed is:

1. In a method for the preparation and analysis of a whole blood sample by photooptical measurement techniques, wherein sample preparation includes enrichment of a non-erythrocyte cellular fraction of the sample by selective stromatolysis of sample erythrocytes with a lytic reagent and labelling of one or more sub-populations of the non-erythrocyte cellular fraction with an indicator labelled binding material which is specific for a characteristic cellular component of a sub-population of the non-erythrocyte cellular fraction, wherein the improvement comprises:

(a) enriching the non-erythrocyte cellular fraction of the whole blood sample and labelling one or more sub-populations of the non-erythrocyte cellular fraction by contacting the sample with an indicator labelled binding material and a lytic reagent system comprising an organic carboxylic acid with a pK greater than 3.0 in a reaction vessel with gentle asymmetric vortex mixing;

(b) transferring an aliquot of selectively stromatolysed sample to a photooptical analyzer without separation of labelled sub-populations of the non-erythrocyte cellular fraction from unconsumed lytic reagent of unbound indicator labelled binding material; and (c) subjecting said aliquot to photooptical analysis.

2. The method of claim 1, wherein sample preparation involves stromatolysis of the erythrocyte fraction of the sample with an effective amount of an acidic lytic reagent, having a pH in the range of from about 2.6 to about 4.0, quenching the activity of said lytic reagent with a companion reagent which is effective in arresting the lytic activity of the lytic reagent and restoring the Ionic Balance of the sample.

3. The method of claim 2 wherein sample preparation involves contacting the sample with reagents concurrent with gentle asymmetric vortex mixing so as to maintain sample particulates at an essentially homogeneous concentration throughout the sample, said preparation requiring less than 90 seconds.

4. The method of claim 2, wherein the sample is contacted with an indicator labelled binding material before the sample is contacted with the lytic reagent.

5. The method of claim 2, wherein the sample is contacted with an indicator labelled binding material concurrent with the lytic reagent.

6. The method of claim 2, wherein the sample is contacted with an indicator labelled binding material after the sample is contacted with the lytic reagent.

7. The method of claim 2, wherein the sample is contacted with a fixative subsequent to staining with the indicator labelled binding material.

8. The method of claim 2, wherein the sample comprises an aged whole blood specimen wherein the endogenous nutrients of the sample have been essentially completely depleted and the cells are fragile.

9. The method of claim 2, wherein the sample comprises a whole blood specimen from a patient suspected of suffering from a disease which involves changes in at least one of non-erythrocyte cellular morphology and population.

10. The method of claim 1, wherein the lytic reagent is an organic acid selected from the group consisting of formic acid, acetic acid, and mixtures thereof.

11. The method of claim 1 in which said selective stromatolysis is accomplished in approximately 10 seconds.

12. The method of claim 11 in which labelling of said non-erythrocyte cellular fraction is effected in about 15 to 60 seconds, prior to said stromatolysis.

* * * * *